United States Patent
Conway

(10) Patent No.: US 6,610,381 B1
(45) Date of Patent: Aug. 26, 2003

(54) ABSORBENT BARRIER SHEET AND METHOD OF MAKING SAME

(75) Inventor: David W. Conway, Mason, OH (US)

(73) Assignee: Standard Textile Co., Inc., Cincinnati, OH (US)

( * ) Notice: Subject to any disclaimer, the term of this patent is extended or adjusted under 35 U.S.C. 154(b) by 977 days.

(21) Appl. No.: 08/853,425

(22) Filed: May 9, 1997

(51) Int. Cl.[7] .............................. B32B 7/04; B32B 27/12

(52) U.S. Cl. .............................. 428/86; 428/88; 428/95; 428/96; 442/304; 442/312; 442/286

(58) Field of Search .............................. 428/86, 88, 95, 428/96; 442/304, 312, 286

(56) References Cited

U.S. PATENT DOCUMENTS

| | | |
|---|---|---|
| 3,065,751 A | 11/1962 | Gobbo, Sr. et al. |
| 3,180,335 A | 4/1965 | Duncan et al. |
| 3,262,451 A | 7/1966 | Morse |
| RE26,151 E | 1/1967 | Duncan et al. |
| 3,322,594 A | 5/1967 | Lucas et al. |
| 3,349,769 A | 10/1967 | Piekarski |
| 3,654,060 A | 4/1972 | Goldman |
| 3,738,362 A | 6/1973 | Sneider |
| 3,763,863 A | 10/1973 | Mesek et al. |
| 3,768,480 A | 10/1973 | Mesek et al. |
| 3,881,490 A | 5/1975 | Whitehead et al. |
| 3,881,491 A * | 5/1975 | Whyte .......................... 128/287 |
| 3,901,240 A | 8/1975 | Hoey |
| 3,903,890 A | 9/1975 | Mesek et al. |
| 3,916,900 A | 11/1975 | Breyer et al. |
| 3,921,639 A | 11/1975 | Cepuritis |
| 3,967,623 A | 7/1976 | Butterworth et al. |
| 3,974,308 A | 8/1976 | Winters |
| 4,045,833 A | 9/1977 | Mesek et al. |
| 4,051,848 A | 10/1977 | Levine |
| 4,077,410 A | 3/1978 | Butterworth et al. |
| 4,097,943 A | 7/1978 | O'Connell |
| 4,102,340 A | 7/1978 | Mesek et al. |
| 4,173,046 A | 11/1979 | Gallagher |
| 4,210,144 A | 7/1980 | Sarge, III et al. |
| 4,282,874 A | 8/1981 | Mesek |
| 4,285,343 A | 8/1981 | McNair |
| 4,333,463 A | 6/1982 | Holtman |
| 4,338,938 A | 7/1982 | Seavitt |
| 4,372,312 A | 2/1983 | Fendler et al. |
| 4,388,075 A | 6/1983 | Mesek et al. |
| 4,496,358 A | 1/1985 | Karami et al. |
| 4,524,474 A | 6/1985 | Svensson |

(List continued on next page.)

FOREIGN PATENT DOCUMENTS

| | | |
|---|---|---|
| DE | 9413900 | 12/1994 |
| DE | 29600123 | 4/1996 |
| EP | 496567 | 7/1992 |
| WO | WO95/04654 | 2/1995 |

Primary Examiner—Cheryl A. Juska
(74) Attorney, Agent, or Firm—Wood, Herron & Evans, LLP

(57) ABSTRACT

An absorbent barrier sheet (10) includes an integral fabric web (12) and a vinyl barrier material (14) intimately connected to and across the integral fabric web (12). The web (12) includes an upper portion (16) and a lower portion (18), with the upper portion including a plurality of hydrophobic first yarns (20) and the lower portion including a plurality of fluid-retaining second yarns (22). In addition, the web (12) has a middle portion (24) which includes a set of ground yarns (26) and parts of the hydrophobic and fluid-retaining yarns (20),(22), with the ground yarns (26) integrating the hydrophobic and fluid-retaining yarns (20), (22) of the upper and lower portions (16), (18), thereby forming the integral fabric web (12). The vinyl barrier material (14) is intimately connected to and across the fluid-retaining lower portion (18) of the integral fabric web (12). In this fashion, fluid at the top of the absorbent barrier sheet (10) tends to wick downward towards the fluid-retaining portion (18), whereby the top of the sheet tends towards dry. And because the sheet (10) includes the vinyl barrier material (14), the bottom of the sheet (10) remains dry.

22 Claims, 2 Drawing Sheets

U.S. PATENT DOCUMENTS

| | | | |
|---|---|---|---|
| 4,573,991 A | * 3/1986 | Pieniak et al. | 604/385.1 |
| 4,650,481 A | 3/1987 | O'Connor et al. | |
| 4,681,577 A | 7/1987 | Stern et al. | |
| 4,685,914 A | 8/1987 | Holtman | |
| 4,781,710 A | 11/1988 | Megison et al. | |
| 4,798,603 A | 1/1989 | Meyer et al. | |
| 4,886,511 A | * 12/1989 | Korpman | 604/365 |
| 4,961,982 A | * 10/1990 | Taylor | 428/41 |
| 5,009,652 A | 4/1991 | Morgan et al. | |
| 5,012,540 A | 5/1991 | Hockaday | |
| 5,019,073 A | 5/1991 | Roessler et al. | |
| 5,034,264 A | 7/1991 | Wagner et al. | |
| 5,065,600 A | 11/1991 | Byles | |
| 5,085,653 A | 2/1992 | Levy | |
| 5,091,240 A | 2/1992 | Kajander et al. | |
| 5,098,423 A | * 3/1992 | Pieniak et al. | 604/385.1 |
| 5,275,591 A | 1/1994 | Mavinkurve | |
| 5,290,269 A | * 3/1994 | Heiman | 604/378 |
| 5,383,869 A | * 1/1995 | Osborn, III | 604/385.1 |

* cited by examiner

ABSORBENT BARRIER SHEET AND METHOD OF MAKING SAME

BACKGROUND OF THE INVENTION

I. Field of the Invention

The present invention relates to durable and launderable absorbent sheets and particulary to such absorbent sheets in which the upper, fluid receiving surface presents a generally dry feel even after fluid is placed thereon, and yet which has a generally dry bottom side as well.

II. Description of Prior Art

One highly successful absorbent barrier sheet has been marketed by Standard Textile Co., Inc, of Cincinnati, Ohio, as an incontinent pad. In that pad, the upper ply of material is provided by an integral fabric web having a hydrophobic upper surface and a fluid absorbing lower surface into which fluid at the upper surface will wick so as to present a generally dry feel. The fabric web is marketed as Comply® material by Standard Textile. The bottom of the incontinent pad includes a barrier layer to thus also present a dry surface. In order to provide a surface to which the barrier may be attached without destroying the fluid absorbency of the Comply® web, and to provide rigidity to the pad, there is also included a layer of nonwoven felt between the barrier layer and the top fabric web. In order to stabilize the pad such as during washings and the like, the felt is attached to the Comply® fabric such as by quilting, and also to the barrier layer such as by adhesive lamination.

The cost of making a sheet like the incontinent pad is significant including as it does several different plies and manufacturing steps. Moreover, the multiple plies, and particularly the felt, make the sheet relatively thick. Thus, that type of sheet is not economical for retail and consumer usage and so has been primarily limited to institutional medical usage.

SUMMARY OF THE INVENTION

The present invention provides an absorbent barrier sheet that is more economical to produce, relatively thin, and with broad application to a variety of retail and consumer usages as well as institutional usages. To this end, and in accordance with the principals of the present invention, the barrier layer is connected directly to the fluid absorbing portion of the integral fabric web, which surprisingly has not had a deleterious impact on absorbency. The fluid barrier material at the bottom of the sheet is intimately connected to and across the lower fluid-retaining portion of the fabric web so as not to require any intervening layers or manufacturing steps to couple the barrier layer to the integral hydrophobic/fluid absorbent web. In this fashion, fluid which comes in contact with the top of the sheet wicks down along the yarns of the hydrophobic upper portion toward the yarns of the lower fluid-retaining portion, where the fluid is absorbed so as to present a generally dry upper surface. And because the sheet includes a fluid barrier material connected across this fluid-retaining lower portion, fluid is generally prevented from passing through this barrier material, thereby keeping the bottom of the sheet as well as any underlying surface dry. Moreover, because the barrier is intimately connected to the integral fabric web, manufacture of the sheet is simple and cost effective.

If desired, the hydrophobic upper portion of the barrier sheet web may be formed of synthetic yarns while the lower fluid-retaining portion may be formed of natural yarns. In addition, the barrier material advantageously is vinyl, either extrusion coated or laminated onto the lower fluid-retaining portion of the integral fabric web. The barrier material may form the technical bottom of the absorbent barrier sheet, in which case the exposed bottom surface of the barrier material may be embossed so as to form an aesthetically pleasing pattern. Alternatively, the technical bottom of the absorbent barrier sheet may be a second fabric web intimately connected to the fluid barrier material on the side of the barrier material opposite the lower fluid-retaining portion of the integral fabric web.

In accordance with a further aspect of the invention, the absorbent barrier sheet is formed or incorporated into any of a number of different products. In fact, the sheet may be used wherever it is desirable to absorb and retain fluids and to have a dry bottom surface and an upper surface which tends to feel generally dry to the touch. For example, the absorbent barrier sheet is suitably formed as an infant bib, an infant burp cloth, a table cloth or a sheet to be placed under serving dishes, indoor plants and the like. In addition, the sheet is suitably incorporated into incontinent or other fluid discharge products, such as incontinent pads, diapers, infant t-shirts and adult undergarments, for example.

By virtue of the foregoing, there is thus provided an economical, relatively thin absorbent sheet which is capable of absorbing fluids and preventing those fluids from passing to a surface below, while also presenting a generally dry upper face at the top of the sheet. In addition, because of its characteristics, the sheet is suitable for numerous uses, as noted above. These and other objects and advantages of the present invention shall be made apparent from the accompanying drawings and description thereof.

BRIEF DESCRIPTION OF THE DRAWINGS

The accompanying drawings, which are incorporated in and constitute a part of this specification, illustrate embodiments of the invention and, together with the general description of the invention given above and the detailed description of the drawings given below, serve to explain the principles of the invention.

DETAILED DESCRIPTION OF THE DRAWINGS

Figure 1A:
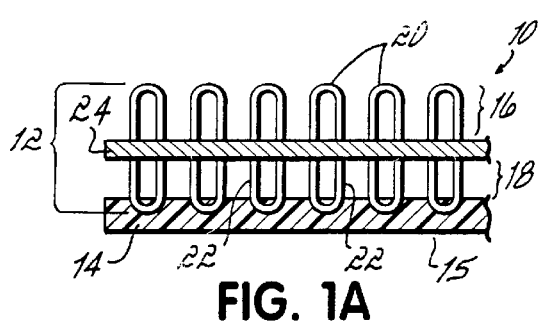
FIG. 1A is a schematic, cross-sectional view of the embodiment of an absorbent barrier sheet in accordance with the principles of the present invention.

With reference to FIG. 1A, an embodiment of the absorbent barrier sheet 10 according to the principles of the invention is shown having an integral fabric web 12 intimately connected to a polymeric fluid barrier material 14. The integral fabric web 12 may be a length of Comply® fabric which includes an upper hydrophobic portion 16 and a lower fluid-retaining portion 18 in wicking relationship to the upper portion 1,6. To this end, the upper portion includes a plurality of hydrophobic, typically synthetic, first yarns 20 (such as polyester or polypropylene yarns of 168 denier) formed in a loop-pile construction, and the lower portion includes a plurality of second yarns 22 which also are formed in a loop-pile construction. The second yarns 22 preferably are hydrophilic (such as cotton yarns of 18 singles). Additionally, integral fabric web 12 has a middle or ground portion 24 which includes a set of ground yarns (not shown) (such as 50/50 polyester/cotton blended yarn) and parts of the hydrophobic and hydrophilic yarns 20, 22 (not shown), with the ground yarns serving to integrate the hydrophobic and hydrophilic yarns 20, 22 of the upper and lower portions 16, 18 into a single-ply fabric layer 12. This general construction is described in Heiman U.S. Pat. No. 5,290,269 and Byles U.S. Pat. No. 5,065,600, the disclosures of both of which are incorporated herein in their entirety by reference. The web 12 may also be a channeled fabric as shown in my co-pending U.S. patent application Ser. No. 08/682,142, entitled "Absorbent Fabric and Undergarments Incorporating the Fabric," filed Jul. 17, 1996, now U.S. Pat. No. 5,906,876, May 25, 1999 the disclosure of which is incorporated herein in its entirety by reference.

Figure 1B:
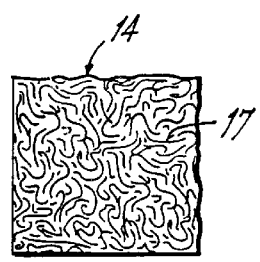
FIG. 1B is a schematic bottom view of the sheet of FIG. 1A.

The fluid barrier material 14 (such as vinyl or polyurethane, for example) is intimately connected to and across the lower portion 18 of the integral fabric web 12, with the barrier material having a face 15 opposite the fabric web lower portion 18. The upper portion 16 of web 12 defines the top of sheet 10. In the embodiment shown in FIG. 1A, opposite face 15 of barrier 14 forms the bottom of the sheet 10, in which event, face 15 may include an embossed pattern 17 as shown in FIG. 1B. Barrier material 14 is advantageously a vinyl, such as polyvinyl chloride (PVC), for example, and the present invention will be described in further detail below using vinyl as the barrier material. As used herein, the term "vinyl" refers to any polymeric barrier material including the vinyl monomer. It will be kept in mind, however, that the barrier material may be other than vinyl as long as it is a fluid resistant or fluid proof material capable of intimate connection to the lower portion of the integral fabric web, as will be understood by one of ordinary skill upon a review of this detailed description. An example is polyurethane, although other barrier materials may be used.

Figure 1C:
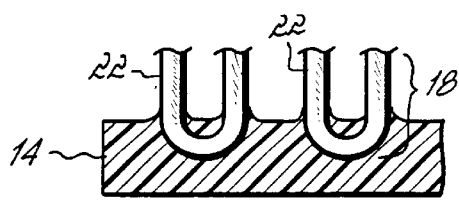
FIG. 1C is an enlarged view of a portion of the sheet of FIG. 1A showing one version of the sheet, wherein the barrier material migrates into aspects of the fabric web lower portion.
Figure 1D:
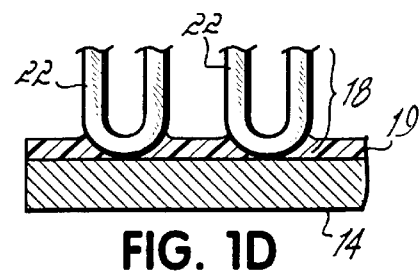
FIG. 1D is a view similar to FIG. 1C showing another version of the sheet wherein the barrier material is held to the fabric web lower portion by an adhesive.

Barrier material 14 typically may be applied to lower portion 18 of fabric web 12 either by a coating or extrusion process, or by a lamination process, as will be described in greater detail below. As shown in FIG. 1C, when barrier material 14 is coated onto integral fabric web 12 in a generally liquid state, the material 14 migrates into aspects of the fabric web lower portion 18. Such migration may include, for example, migration into and/or around portions of the second yarns 22 of the fabric web lower portion 18. The liquid then sets to connect the barrier material 14 to web 12. Alternatively, the barrier material 14 may be a separate, typically solid web held to the fabric web lower portion 18 such as by lamination. To this end, and as shown in FIG. 1D, an adhesive 19 is used to intimately connect the web of barrier material 14 to the fabric web lower portion 18.

Figure 2:
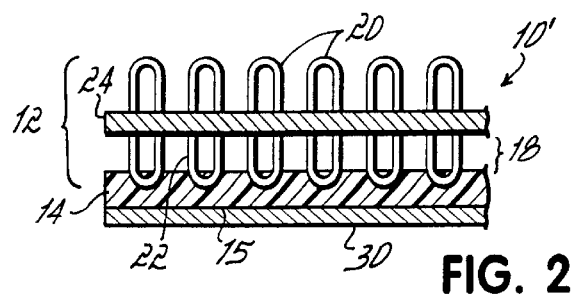
FIG. 2 is a schematic, cross-sectional view of another embodiment of an absorbent barrier sheet in accordance with the principles of the present invention.

With reference to FIG. 2, a second embodiment 10' of an absorbent barrier sheet of the present invention is shown having the integral fabric web 12 and the fluid barrier material 14 intimately connected to and across the fabric web lower portion 18 all as above-described, and with a second fabric web 30 (for example, a polyester or rayon scrim, or a polyester brushed tricot), intimately connected to and across the opposite face 15 of the barrier material 14. Thus, while barrier material 14 is at the bottom of the sheet 10', fabric web 30 actually defines the bottom of sheet 10'.

Figure 3:
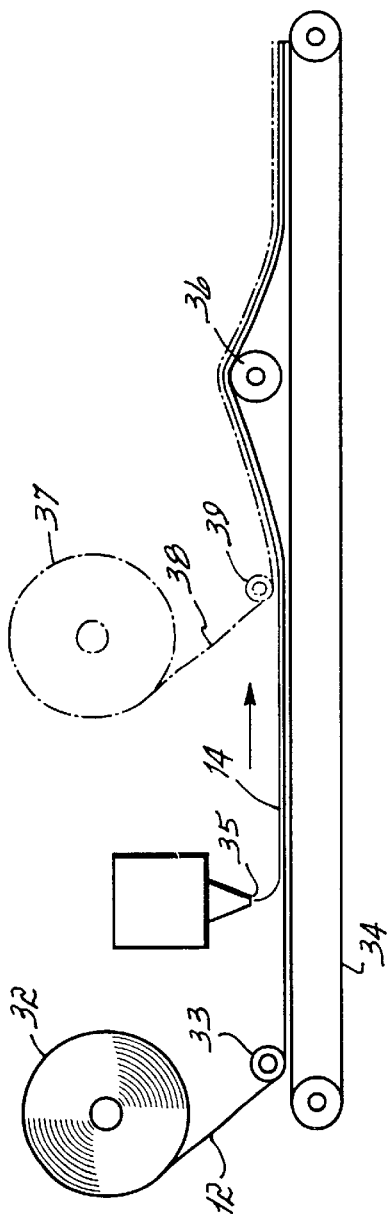
FIG. 3 is a schematic illustration of a method of forming the sheet of FIGS. 1A and 2.

The absorbent barrier sheets of the present invention may be formed in any of a number of ways, an example of which is an extrusion process as will be discussed with reference to FIG. 3. Integral fabric web 12 is fed from a roll or spool 32 containing the fabric 12, around a tensioning bar or bars 33, to a conveyer 34, with the lower fluid-retaining portion of the fabric web oriented (upwardly in FIG. 3) so as to receive completely thereacross an extrusion coating of liquid barrier material 14 (e.g. vinyl or polyurethane) from an extrusion orifice 35. After barrier material 14 is applied, the coated fabric is passed over a chilled roller 36 to assist in curing the liquid barrier material 14. After material 14 is cured, the completed barrier sheet 10 is wound onto a spool (not shown) at the opposite end of the conveyor. Where the barrier material is vinyl, it may be extruded in an amount from about 8 oz./yd.$^2$ to about 12 oz./yd.$^2$, and advantageously in an amount of about 10 oz./yd.$^2$.

While it is possible to form an absorbent barrier sheet by applying a single extruded coating of the vinyl barrier material onto the fluid-retaining portion 18 of the integral fabric web 12, the application of only a single coating may result in pin holes in the vinyl barrier material, depending upon the particular integral fabric web, vinyl and vinyl thickness used. Accordingly, when the extrusion coating method is used, it may be desirable to apply the vinyl barrier material in a two-pass extrusion process. For example, a suitable extrusion-coated product may be achieved by initially extruding a 5 oz./yd.$^2$ coat onto web 12, followed by a second extrusion coat of 5 oz./yd.$^2$. Depending upon the particular extrusion machine being used, once the first coat has been applied, this coat typically is cured and the coated fabric is wound onto a spool (not shown). This "first-pass" roll thus created then may be reloaded at the front of the conveyor for a second pass through the extrusion coating equipment to receive the second coating of vinyl over the first coating. The two passes of coating effectively merge into a single barrier material as that term is used herein. Additionally, integral fabric web 12 is advantageously provided in a finished state (i.e. having been bleached and heat set) as opposed to a gray state (i.e. without bleaching and heat setting), in order to enhance the longevity of the product through numerous wash cycles. If an embossed pattern is desired on the bottom surface 15 of the vinyl barrier material 14, an embossing pattern 17 (as shown in FIG. 1B) may be formed in that surface before it is cured, for example by passing the extruded coating under a roller (not shown) having an embossing pattern prior to, or with, the chilled roller 36. Suitable vinyls (for example, "V-Care Formula 28") are available from Vintex, Inc., One Mount Forest Drive, Mount Forest, Ontario, Canada N0G 2L0.

An extrusion coating process also may be used to form an embodiment of the absorbent barrier sheet 10' which includes additional fabric web 30 at the bottom face of the sheet, as shown in FIG. 2. If desired, this embodiment of the barrier sheet 10' may be formed by first extruding a single coating of liquid barrier material 14 onto one side of the fabric web 30 (not shown). This step may be carried out using the same or similar extrusion apparatus as discussed above in conjunction with the formation of extrusion-coated barrier sheet 10. For example, fabric web 30 may be fed from a roll to a conveyor, where a liquid barrier material 14 is extruded onto one face of the fabric web 30. The coating typically is applied in an amount of about 8 oz./yd.$^2$ to about 12 oz./yd.$^2$, and advantageously in an amount of about 10 oz./yd.$^2$. The coated fabric web then may be passed over a chilled roller to assist in curing the barrier material 14, at which point, the coated fabric web 38 (shown in phantom line in FIG. 3) may be wound onto another spool 37 (also shown in dotted line in FIG. 3). Spool 37 of coated fabric web 38 is positioned near the extrusion coating conveyor, so that web 38 may be joined with the integral fabric web 12 as discussed in detail below. In particular, integral fabric web 12 may be fed from a roll 32 to the conveyor 34, as shown in FIG. 3, where the fluid-retaining portion of the fabric web 12 receives a single-pass extrusion coating of liquid barrier material 14 from the extension orifice 35. The coating typically is applied in an amount of about 8 oz./yd.$^2$ to about 12 oz./yd.$^2$, and advantageously in an amount of about 10 oz./yd.$^2$. At a point beyond the extrusion orifice 35, coated fabric web 38 is fed from spool 37, around a tensioning bar or bars 39, and down onto the freshly extrusion-coated fabric web 12, with the barrier material side of coated web 38 facing and contacting the just-applied, still fluid, barrier material 14 on the fabric web 12. These layers then may be passed over chilled roller 36 (shown in dotted line), as well as pressure-applying rollers (not shown) as is understood in the art, with the just-applied barrier material 14 becoming cured, thereby forming absorbent barrier sheet 10'.

Figure 4:
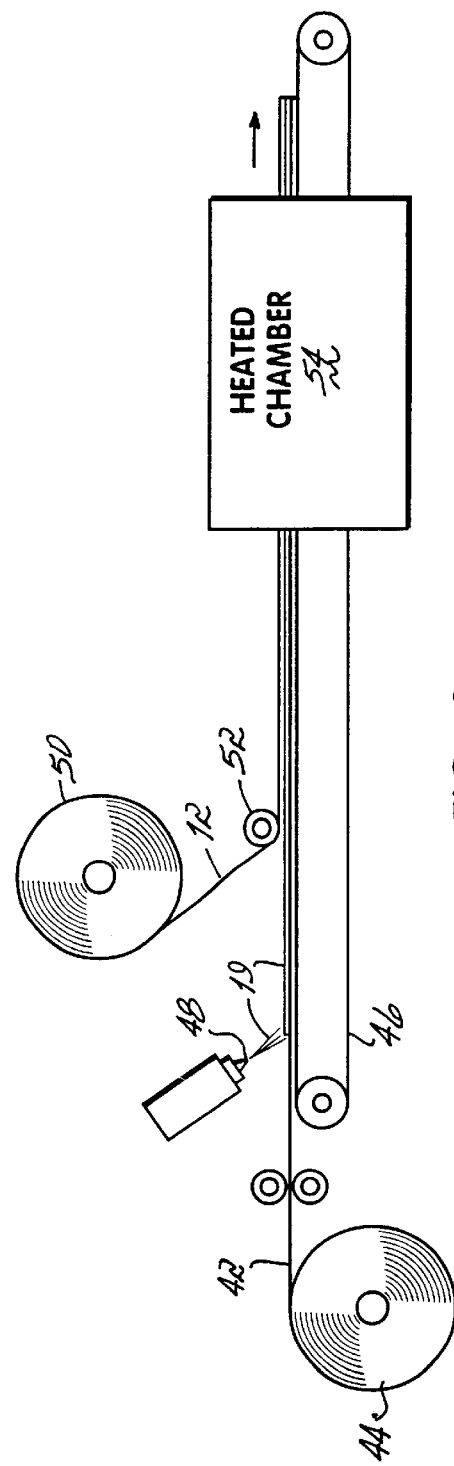
FIG. 4 is a schematic illustration of another method of forming the sheet of FIGS. 1A and 2.

Alternatively, the absorbent barrier sheets 10 and 10' may be formed by laminating the vinyl barrier material 14 to the absorbent lower portion of the integral fabric web 12. With reference to FIG. 4, the vinyl barrier material 14 is provided in the form of a polymeric sheet or web 42 from a roll 44 (or as a spool 37 of web 38 is as above described) which pays out to a conveyor 46 and to an adhesive spray nozzle 48 which sprays liquid adhesive 19 onto the exposed surface of the polymeric sheet 42. Alternatively, adhesive may be applied by passing the exposed surface of the polymeric sheet 42 across an adhesive-applying roller positioned within a bath of adhesive (not shown), as is known in the art. A roll 50 of web 12 is paid out over adhesive laden sheet 42, guided by a tension bar or bars 52, such that the lower fluid-retaining portion of the fabric web 12 is brought into intimate contact with adhesive 19, to form sheet 10. Sheet 10 then passes through a heated chamber 54 which includes heated rollers that apply pressure to the barrier sheet 10 to complete the adhesion process. When absorbent barrier sheet 10' is desired, the integral fabric web 12 and barrier material 14 may be adhesively laminated as discussed immediately above, thereby forming barrier sheet 10. This sheet 10 may be wound on a spool (not shown) and reloaded at the front of the conveyor 46 of FIG. 4, positioned, for example, where roll 44 is shown, and with the vinyl barrier side facing toward the particular adhesive applicator (such as the spray nozzle 48 shown, an adhesive-laden roller or other applicator). The fabric web 30 (not shown) for use in forming the technical bottom of barrier sheet 10' may be loaded near the conveyor 46 of FIG. 4, positioned, for example, where roll 50 is shown. In this orientation, sheet 10' then may be formed by feeding what is effectively sheet 10 (not shown) to the conveyor 46, coating the exposed vinyl barrier side with adhesive, feeding the fabric web 30 down onto the freshly applied adhesive surface, and passing the barrier sheet 10' through the heat chamber. Suitable vinyl sheeting (for example, F-17 Modified Film) and adhesives (for example, Duracoat-formulated laminating Plastisol adhesive) are available from Duracoat, located at 350 North Diamond Street, Ravenna, Ohio 44266. Although vinyl sheeting of different thicknesses may be used, vinyl sheeting having a thickness of approximately 4 mil (four thousandths of an inch) may be used advantageously. In addition, as is true in the extrusion coating process, the integral fabric web is advantageously provided in a finished state, i.e., having been bleached and heat set, prior to the lamination step.

If desired, other types of adhesives may be used in the lamination process. For example, a dry adhesive in the form of a polymeric web may be used. In such a case, the adhesive web may be fed from a roller and "sandwiched" between integral fabric web 12 and fluid barrier material 14. The adhesive lamination may be completed by exposing the combined layers to appropriate temperature and pressure conditions, as will be understood by one of ordinary skill in the art. A suitable dry adhesive web is Bostic PE-20 available from John Boyle & Co., Inc., 1803 Salisbury Road, Statesville, N.C. 28687. When such a dry adhesive web is used, a vinyl layer having a thickness of about 4 mil may work.

If an embossed pattern is desired on the bottom surface of the vinyl barrier material, an embossing pattern 17 may be formed in that surface during the initial formation of the polymeric vinyl sheet 42 prior to the lamination step.

In use, when fluid comes in contact with the hydrophobic yarns 20 at the top of the sheet 10 or 10', the fluid wicks down along the length of these yarns 20 toward and into the middle portion 24 where the fluid contacts portions of the hydrophilic yarns 22. From this middle portion 24, fluid migrates into and is absorbed by the hydrophilic yarns 22 of the lower portion 18, thereby presenting a generally dry-to-the-touch feel at the top of the sheet 10. In addition, because the fluid barrier material 14 is intimately connected to and across the lower portion 18 of the fabric web 12, fluid held in the absorbent yarns 22 of the lower portion 18 does not pass through the barrier material 14, and the sheet 10 presents a dry feel at its bottom.

Figure 5:
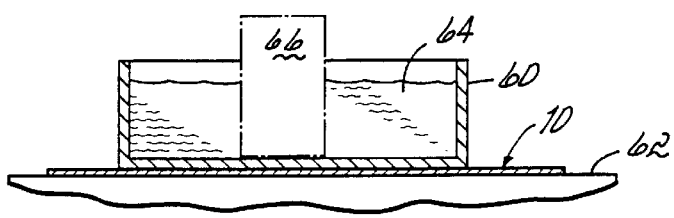
FIG. 5 is a schematic, cross-sectional view of the absorbent barrier sheet of FIG. 1A in use, with the sheet disposed between a container and a supporting surface.

The absorbent sheets of the present invention may be used to advantage wherever it is desirable to have a material which absorbs and retains fluid, yet which inhibits or prevents the fluid from passing through to a surface below, and which tends towards dry at the top face. With reference to FIG. 5, the absorbent barrier sheet 10 (or 10') is shown positioned between a container 60 and a support surface 62. The container 60 itself holds a fluid 64 and also may include an object 66. For example, the container 60 may be a pot holding an object 66 such as a plant on a countertop 62, or a Christmas tree stand for holding the trunk 66 of a Christmas tree positioned on the floor 62. Alternatively, container 60 may be a serving dish containing a hot food item 66 on a dining room table 62. As will thus be readily understood by one of ordinary skill in the art, the absorbent barrier sheet of the present invention has numerous applications. Regardless of the particular use, if water from a watering pitcher, or fluid from a serving dish, or other fluids are spilled or sloshed onto a support surface 62, such as a floor or table, in the absence of the absorbent barrier sheet, the floor, the dining room table or the like may become damaged. However, when the absorbent barrier sheet 10 is positioned on top of the particular support surface 62, as shown in FIG. 5, any spill is readily wicked by the yarns of the hydrophobic upper portion downward towards the yarns of the lower fluid-retaining portion where the fluid is held. Similarly, the vinyl barrier material intimately connected to and across the fabric web lower portion keeps fluid held in the fluid-retaining portion from passing through the sheet onto the underlying support surface. In addition, because the top of the sheet consists of yarn portions which are hydrophobic, the upper face of the sheet tends towards dry, particularly after the spilled fluid has had an opportunity to wick downward into the underlying absorbent portion of the integral fabric web. When the sheet is used as a picnic blanket (when surface 62 is the ground, for example), it not only has the advantage of absorbing spills from above, but the barrier material (particularly vinyl) also prevents moisture from passing upward from the ground.

Figure 6:
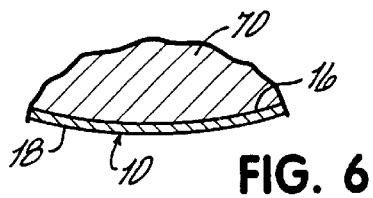
FIG. 6 is a schematic, cross-sectional view of the absorbent barrier sheet of FIG. 1A disposed against a surface of a body.

Additional examples illustrating some of the many other uses of the absorbent barrier sheet include an infant bib or burp cloth, as well as various products for managing incontinence and/or other bodily fluid discharge. With reference to FIG. 6, the sheet 10 (or 10') is shown disposed against a portion of a human or animal body 70, with the hydrophobic upper portion 16 of the sheet oriented toward the body. If desired, the sheet may be formed as an incontinent pad by appropriate edge treatment, or incorporated into a garment, such as a diaper, as shown for example in Heiman U.S. Pat. No. 5,290,269. Alternatively, the sheet may be incorporated into an infant t-shirt or undergarment, as shown in my copending application Ser. No. 08/575,623, entitled "Infant T-Shirt", filed Dec. 20, 1995 now U.S. Pat. No. 5,819,317, Oct. 13, 1998, and Ser. No. 08/597,132, entitled "Hygienic Panty and Quick-Attach Pad", filed Feb. 6, 1996 now U.S. Pat. No. 5,778,457 (Jul. 14, 1998) respectively, both of which are incorporated herein in their entirety by reference. Depending upon the particular application, the sheet may be formed to cover the majority of the body-contacting surface of the pad or undergarment, or may be formed into a more limited portion of the garment, such as the crotch panel.

While the present invention has been illustrated by description of embodiments, and while the illustrative embodiments have been described in considerable detail, it is not the intention of the inventor to restrict or in any way limit the scope of the appended claims to such detail. Additional advantages and modifications will readily appear to those skilled in the art. For example, although the upper and lower portions of the integral fabric web discussed above have been formed as pile loops, the upper and lower portions may be formed or finished in any particular manner, as long as the resulting material is an integral fabric web. With respect to the yarns used in forming the hydrophobic upper portion, in addition to the polyester and polypropylene discussed above, examples of other suitable yarns include nylon, as well as yarns which are chemically treated so as to acquire hydrophobic properties. With respect to the yarns of the lower fluid-retaining portion, any yarns may be used as long as they are less hydrophobic than the yarns of the upper portion. In addition to the cotton yarns described above, other yarns such as rayon, acrylic, acetate or Lyocell (a solvent-spun cellulose fiber available from Courtaulds Fibers Inc., P.O. Box 141, Axis, Ala. 36505), for example, may be used. In addition, other yarns may be used which are chemically treated so as to have a fluid absorbent or hydrophilic quality. With respect to the fluid barrier material, although vinyl has been described in detail above, any fluid resistant or fluid proof material capable of being intimately connected to the lower fluid-retaining portion of the integral fabric web may be used. Examples of such additional fluid barrier materials include polyurethane, polytetrafluoroethylene, silicone and rubber. And in the embodiments of the sheet which includes a fabric layer at the bottom of the sheet, this fabric layer need not be limited to a polyester or rayon scrim, or a polyester tricot. Instead, the material used for this fabric layer may be any fabric capable of being connected to the fluid barrier material. In addition, if desired, a fragrance may be added to one or more components of the sheet to impart a characteristic scent. For example, a fragrance may be added to the vinyl barrier material, preferably when the vinyl is extruded or formed into a separate web. In addition, the absorbent barrier sheet may be provided with an antimicrobial treatment or with yarns which contain an antimicrobial agent, as shown, for example, in my concurrently filed U.S. Patent Application entitled "Reusable Fluid-Absorbent Integrated Textile Sheet With Anti-Microbial," the disclosure of which is incorporated herein by reference. The invention in its broader aspects is therefore not limited to the specific details, representative apparatus and methods, and illustrative examples shown and described. Accordingly departures may be made from such details without departing from the spirit or scope of Applicant's general inventive concept.

Having described the invention, what is claimed is:

1. An absorbent barrier sheet comprising:
    an integral fabric web having a generally hydrophobic upper portion at the top of the sheet, the fabric web having a lower fluid-retaining portion in wicking communication with the upper portion whereby the top of the sheet tends towards dry, the upper portion including synthetic yarns and the lower portion including natural yarns and having a lower surface; and
    a vinyl barrier material intimately connected to substantially the entire lower surface of the fabric web lower portion whereby the bottom of the sheet tends to be dry.

2. The sheet of claim 1 wherein the vinyl barrier material has a face opposite the fabric web lower portion, the opposite face defining the bottom of the sheet.

3. The sheet of claim 2 wherein the barrier material includes an embossed pattern in the opposite face.

4. The sheet of claim 1 wherein the vinyl barrier material has a face opposite the fabric web lower portion, the sheet further including a second fabric web adjacent the opposite face of the vinyl barrier material.

5. The sheet of claim 4 wherein the second fabric web defines the bottom of the sheet.

6. The sheet of claim 1 wherein a portion of the vinyl barrier material is migrated into aspects of the fabric web lower portion.

7. The sheet of claim 1 wherein the vinyl barrier material includes a vinyl web, the sheet further comprising an adhesive holding the vinyl web in intimate connection to and across the fabric web lower portion.

8. An absorbent barrier sheet comprising:
    an integral fabric web having a generally hydrophobic upper portion at the top of the sheet, the fabric web having a lower fluid-retaining portion in wicking communication with the upper portion whereby the top of the sheet tends towards dry, the lower fluid-retaining portion including a lower surface; and
    a barrier material intimately connected to substantially the entire lower surface of the fabric web lower portion whereby the bottom of the sheet tends to be dry.

9. The sheet of claim 8 wherein the barrier material includes vinyl.

10. The sheet of claim 8 wherein the barrier material includes polyurethane.

11. The sheet of claim 8 wherein the lower portion includes natural yarns.

12. The sheet of claim 8 wherein the barrier material has a face opposite the fabric web lower portion, the opposite face defining the bottom of the sheet.

13. The sheet of claim 12 wherein the barrier material includes an embossed pattern in the opposite face.

14. The sheet of claim 8 wherein the barrier material has a face opposite the fabric web lower portion, the sheet further including a second fabric web adjacent the opposite face of the barrier material.

15. The sheet of claim 14 wherein the second fabric web defines the bottom of the sheet.

16. The sheet of claim 8 wherein a portion of the barrier material is migrated into aspects of the fabric web lower portion.

17. The sheet of claim 8 wherein the barrier material includes a web, the sheet further comprising an adhesive holding the web in intimate connection to and across the fabric web lower portion.

18. A method of forming an absorbent barrier sheet comprising the steps of:
   providing an integral fabric web having a generally hydrophobic upper portion and a lower fluid-retaining portion in wicking communication with the upper portion, the lower portion having a lower surface; and
   intimately connecting a barrier material to substantially the entire lower surface of the lower fluid-retaining portion, thereby forming an absorbent barrier sheet with the upper portion at the top of the sheet, and with the barrier material at the bottom of the sheet.

19. The method of claim 18 including extruding the barrier material across the lower fluid-retaining portion to bring it into intimate contact with the lower fluid-retaining portion.

20. The method of claim 18 including laminating the barrier material onto the lower fluid-retaining portion to bring it into intimate contact with the lower fluid-retaining portion.

21. The method of claim 18 wherein the barrier material has a side opposite the fabric web lower portion, the method further comprising providing a second fabric web on the barrier material opposite side to define the bottom of the sheet.

22. An absorbent barrier sheet comprising:
   an integral fabric web having a generally hydrophobic upper portion at the top of the sheet, a lower fluid-retaining portion in wicking communication with the upper portion, and a middle portion defined by an integration boundary of the upper and lower portions of the fabric web, whereby the top of the sheet tends towards dry, the upper portion including synthetic yarns and the lower portion including natural yarns having a lower surface defined by yarn end portions remote from the middle portion of the fabric web; and
   a vinyl barrier material intimately connected to substantially the entire lower surface of the fabric web lower portion, whereby the bottom of the sheet tends to be dry.

* * * * *